United States Patent
Tuthill et al.

(10) Patent No.: US 9,098,614 B1
(45) Date of Patent: Aug. 4, 2015

(54) SYSTEMS AND DEVICES FOR INTERACTIVE, FEEDBACK-DRIVEN EXERCISE

(71) Applicant: Fitweiser, Inc., Las Vegas, NV (US)

(72) Inventors: Steve Tuthill, Eastvale, CA (US); Rudy Campidonica, Las Vegas, NV (US)

(73) Assignee: FITWEISER, INC., Las Vegas, NV (US)

( * ) Notice: Subject to any disclaimer, the term of this patent is extended or adjusted under 35 U.S.C. 154(b) by 0 days.

(21) Appl. No.: 14/329,886

(22) Filed: Jul. 11, 2014

(51) Int. Cl.
*G07F 17/32* (2006.01)
*A63F 13/10* (2006.01)
*G06F 19/00* (2011.01)

(52) U.S. Cl.
CPC .................. *G06F 19/3481* (2013.01)

(58) Field of Classification Search
USPC .............................. 463/30; 700/91
See application file for complete search history.

(56) References Cited

U.S. PATENT DOCUMENTS

| | | | |
|---|---|---|---|
| 2004/0092367 A1* | 5/2004 | Corbalis et al. | 482/54 |
| 2007/0219059 A1* | 9/2007 | Schwartz et al. | 482/8 |
| 2007/0225118 A1* | 9/2007 | Giorno | 482/1 |
| 2009/0098981 A1* | 4/2009 | Del Giorno | 482/9 |
| 2013/0218053 A1* | 8/2013 | Kaiser et al. | 600/595 |
| 2014/0005811 A1* | 1/2014 | Mikan et al. | 700/91 |
| 2014/0149235 A1* | 5/2014 | Gilley et al. | 705/15 |
| 2014/0247151 A1* | 9/2014 | Proud et al. | 340/870.02 |

* cited by examiner

*Primary Examiner* — Pierre E Elisca
(74) *Attorney, Agent, or Firm* — Procopio, Cory, Hargreaves & Savitch LLP; Noel C. Gillespie

(57) ABSTRACT

Systems and devices provide interactive, feedback-driven exercise through reconfigurable exercise devices which provide tactile, visual and auditory feedback, and proactive and reactive resistive control. The reconfigurable exercise device provides motor controlled resistive forces which may be independently controlled to provide active and passive resistance during an exercise. Portable electronic devices in communication with the exercise equipment provide exercise programs, track user activity, communicate with the exercise device to adjust resistance and other exercise parameters in real time, and provide an interactive visual exercise experience using displays and other device feedback. The portable electronic devices may access exercise programs and user profile data from a remote cloud server and connected databases so as to provide a customized and continually updated exercise program to a user at any exercise device in any location.

20 Claims, 7 Drawing Sheets

SYSTEMS AND DEVICES FOR INTERACTIVE, FEEDBACK-DRIVEN EXERCISE

BACKGROUND

1. Field of the Invention

The systems and devices described herein relate generally to interactive exercises, and more specifically to systems and devices which provide interactive, feedback-driven exercises which monitor and interact with a user during an exercise program.

2. Related Art

Existing exercise equipment is limited to simply displaying basic statistics relating to the performance of the user, such as distance traveled, force exerted or calories burned. Exercise devices are designed to perform the same way for every user, allowing minimal customization and providing little if any feedback to the user in relation to the exercise being performed.

As a result, many users also experience gym fatigue from the monotony of exercising in one place with an exercise machine that provides little or no interaction, feedback or entertainment. Although some exercise devices provide connections to audio or video provided by a nearby television or radio station, the content is unrelated to the exercise and has no effect on the user's performance.

Furthermore, while users adopt wearable sensors and electronics to monitor their own health and fitness, exercise devices have failed to integrate or adapt to these new technologies. Users are unable to integrate the information from their exercise devices with the information on their wearable devices, and often cannot integrate the information from their various wearable devices to understand the complete picture of their fitness.

Therefore, what are needed are systems and devices that overcome these significant problems found in the conventional systems as described above.

SUMMARY

Embodiments described herein provide systems and devices for delivering an interactive, feedback-driven exercise through reconfigurable exercise devices which provides physical feedback through proactive and reactive control, as well as portable electronic devices in communication with the exercise equipment to track user activity and provide an interactive visual exercise experience using displays and other device feedback.

In one embodiment, an interactive feedback-driven exercise system comprises an exercise device configured to provide feedback to a user; a portable electronic device in communication with the exercise device to communicate instructions to the user for an exercise program and provide feedback to the exercise device regarding user performance; and a motor controller configured within the exercise device to translate the exercise program and user feedback relating to the exercise program into feedback to the user.

In another embodiment, an interactive reconfigurable exercise device comprises a reconfigurable feedback-driven interaction portion which provides feedback to a user during a performance of at least one exercise program; a visual feedback portion which provides visual feedback to the user relating to the performance of the at least one exercise program; and a controller which communicates with the reconfigurable interaction portion and visual feedback portion to control an amount of the feedback provided by the interaction portion.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide for systems and devices for providing a user with an interactive, feedback-driven exercise through the use of exercise equipment which provides physical feedback through proactive and reactive control, as well as portable electronic devices in communication with the exercise equipment to sense user activity and provide an interactive visual exercise experience using displays and other device feedback.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

I. Interactive Exercise System

Figure 1:
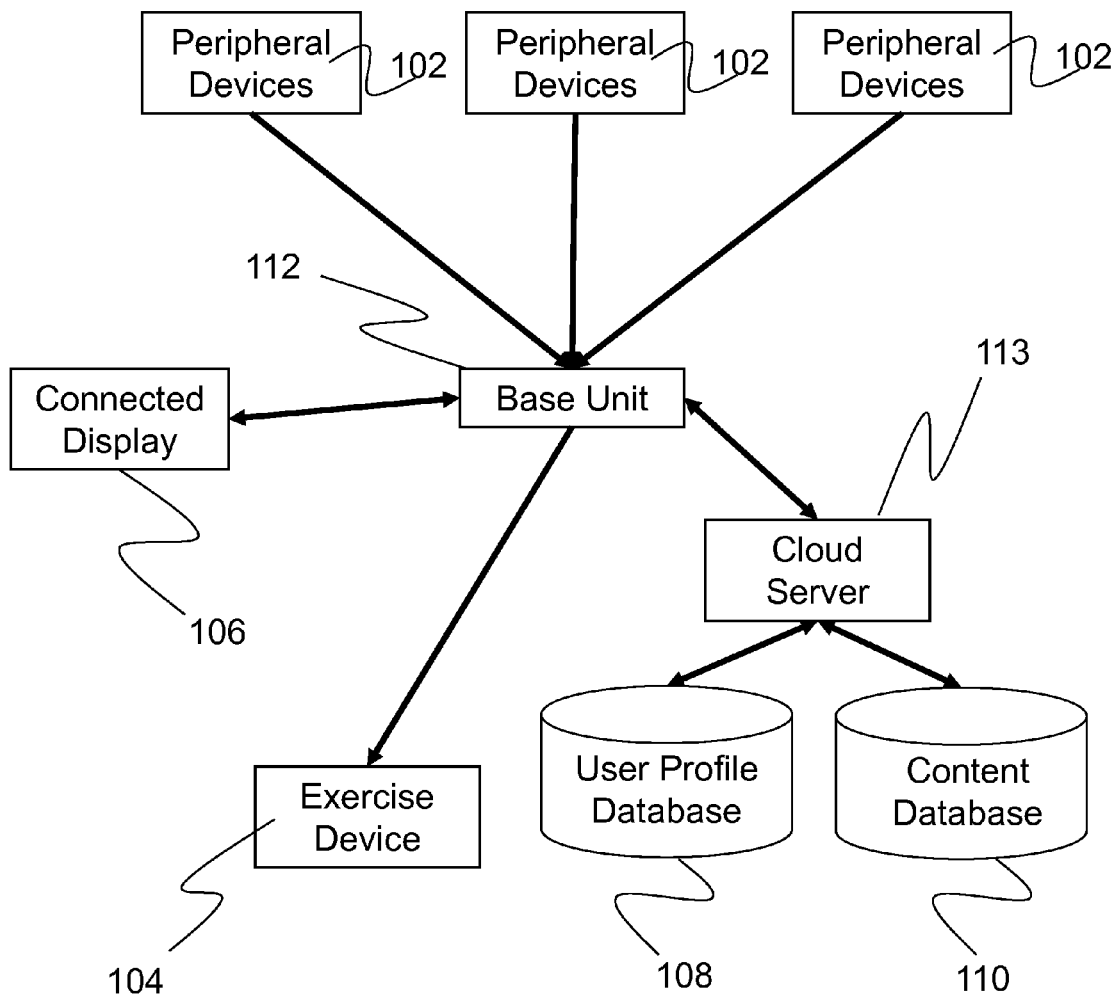
FIG. 1 is a block diagram illustrating an interactive exercise system including an exercise device and a plurality of connected devices and displays, according to an embodiment of the invention.

One embodiment of an interactive feedback-driven exercise system is illustrated in FIG. 1, and includes an exercise device 104 configured to provide feedback to a user; a plurality of peripheral devices 102 in communication with the exercise device 104 to communicate instructions to the user for an exercise program and provide feedback to the exercise device regarding user performance. The exercise device 104 is provided with a motor controller configured within the exercise device to translate the exercise program and user feedback relating to the exercise program into feedback to the user. A base unit 112 may be connected with the exercise device 104 and may be a fixed or portable computing device which controls and manages all of the interactions between the exercise device 104, peripheral devices 102, connected displays 106 and databases 110, as will be described below.

A connected display 106 may be provided to display a graphical user interface to the user during the performance of the exercise program, including information on the user's performance or entertainment information that provides visual interactions with the user to keep the user engaged with the exercise program. For example, the connected display may be a virtual reality display device which provides a virtual reality environment to the user related to the performance of the exercise program.

The exercise device may also be connected with one or more databases which store information, such as a content database 110 which stores information on the content of the exercise programs or a user profile database 108 which stores information on a user profile that is used to configure the exercise programs specifically for each user. The databases may be integrated within the base unit itself, or, as in FIG. 1, accessible via a cloud server 113 at a remote location from the base unit 112.

The peripheral devices 102 may include one or more wearable devices which sense user activity, including motion, physiological data such as heart rate, blood pressure, etc. and report the information back to the exercise device 104 for altering the exercise program based on this feedback.

Figure 2:
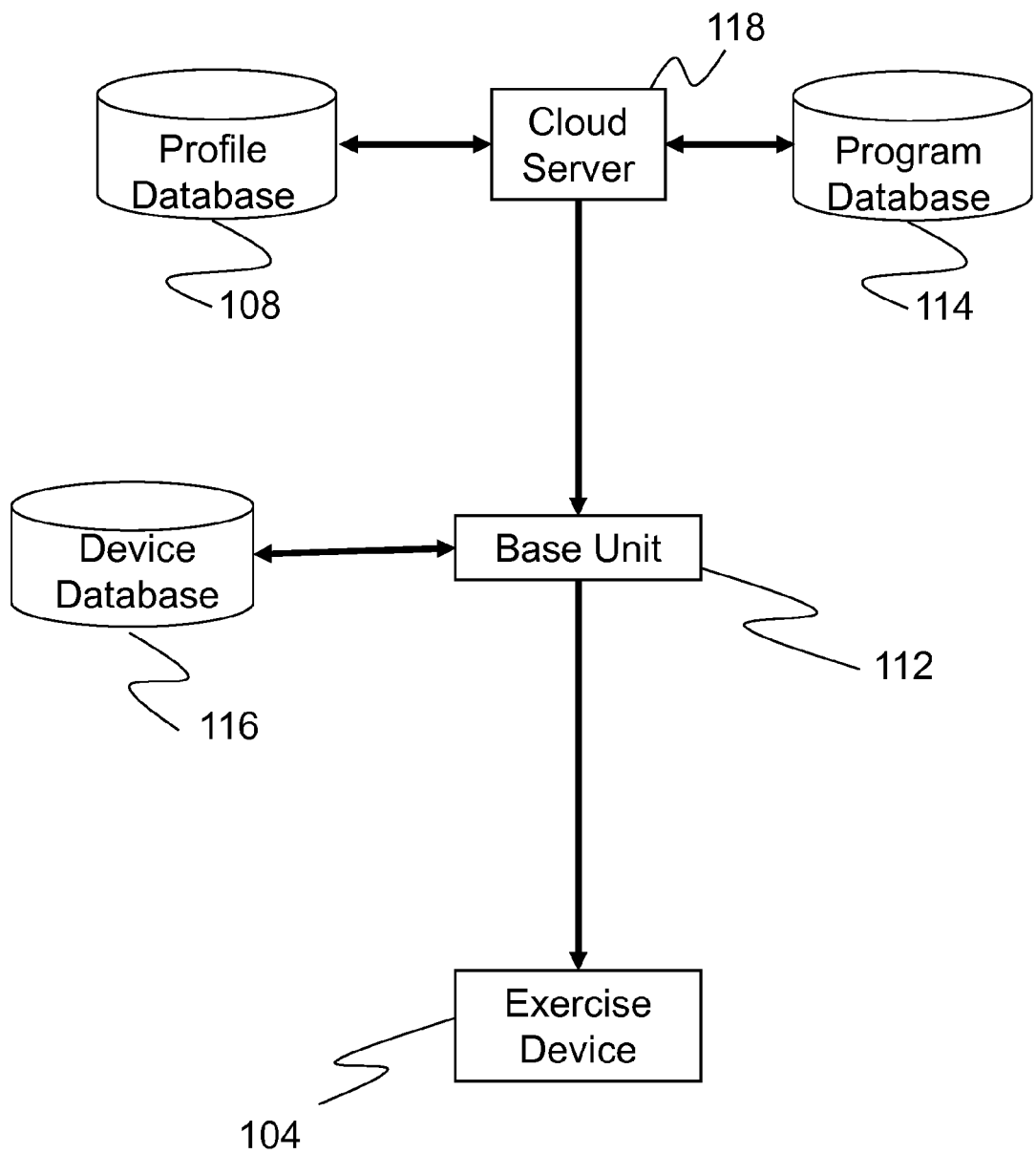
FIG. 2 is a block diagram illustrating a further example exercise system, according to an embodiment of the invention.

An alternate exercise system is illustrated in FIG. 2, where the exercise device is connected with a cloud server 118 that allows the exercise device to access a program database 114 of the exercise programs or the profile database 108 of users and their customized programs. A device database 116 may be connected with the exercise device 104 directly to provide a list of the devices that may be worn by or connected with the users and provide feedback information so that the exercise device 104 can connect with and receive information from these devices during the execution of the exercise program.

II. Peripheral Sensors and Display Devices

In one embodiment, the peripheral devices 102 may be wearable devices and sensors, such as smart watches, bracelets or even sensors embedded into clothing, shoes, etc. The peripheral devices 102 will be configured to communicate with the exercise device 104 and any connected displays 106 to display the user activity during the exercise program. The exercise device 104 may then adjust the feedback provided to the user based on the information obtained from the peripheral sensors to either increase or decrease resistance, difficulty, etc.

The connected display 106 may include display devices such as a smartphone, tablet, computing device, television or monitor, virtual reality display such as goggles or eyeglasses, etc. that provide visual information to the user. The connected display may be incorporated into the exercise device or remotely mounted at a separate location in the area, or, as with a virtual goggles device, worn by the user.

III. Feedback Exercise Device

Figure 3:
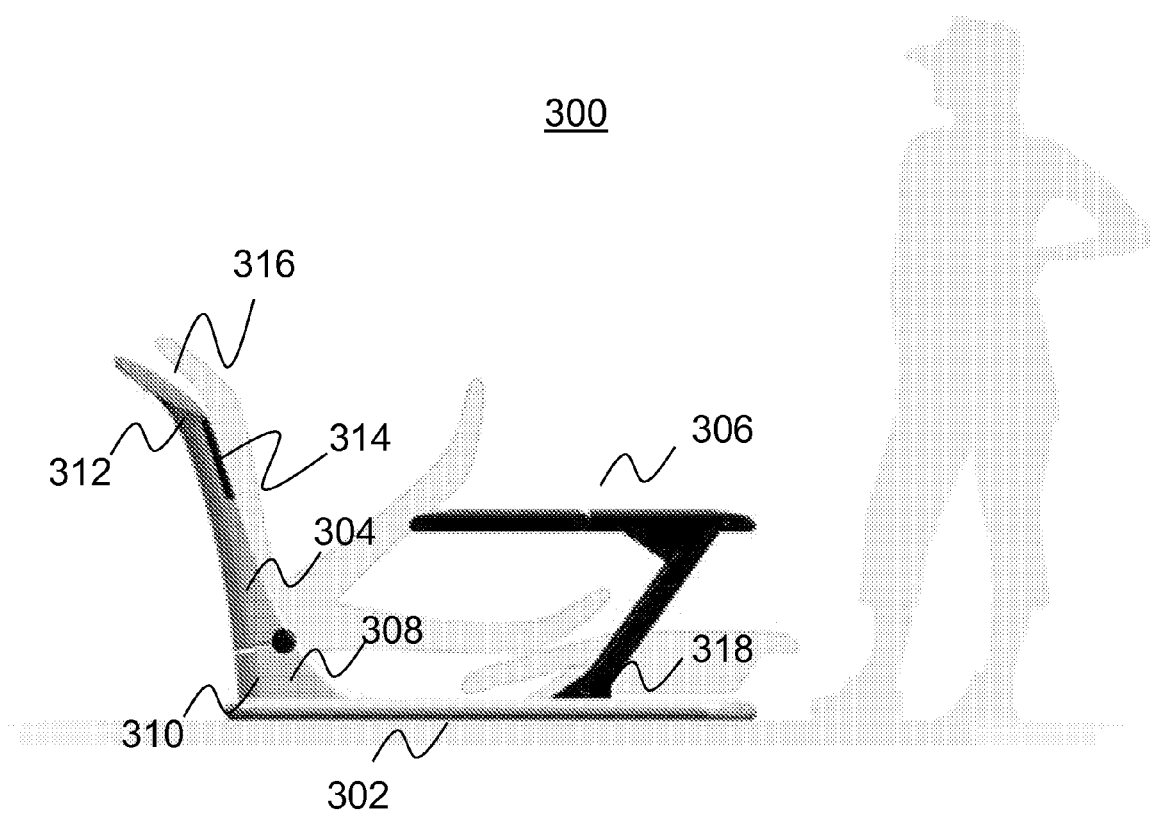
FIG. 3 is an side-view illustration of an example exercise device, according to an embodiment of the invention.
Figure 4:
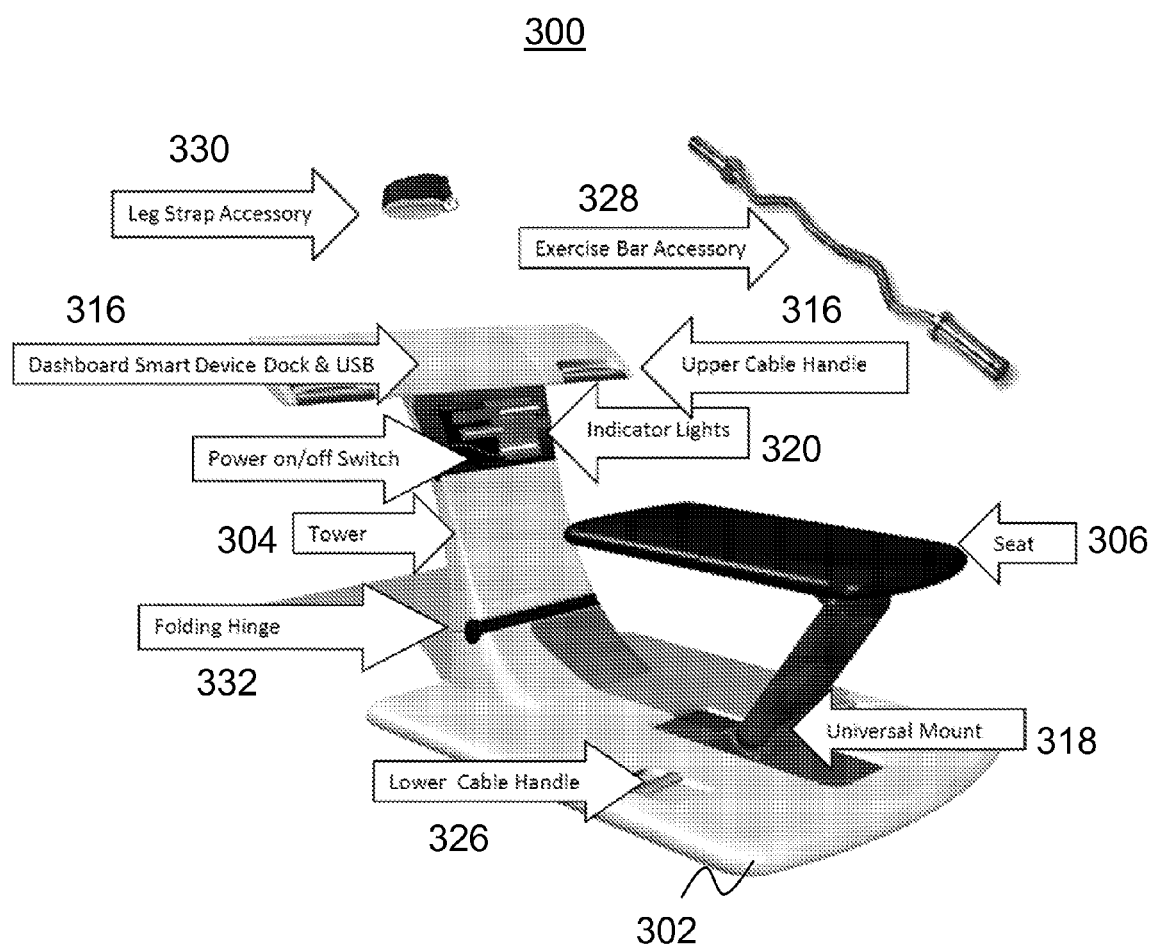
FIG. 4 is a perspective-view illustration of a first configuration of the exercise device, according to an embodiment of the invention.
Figure 5:
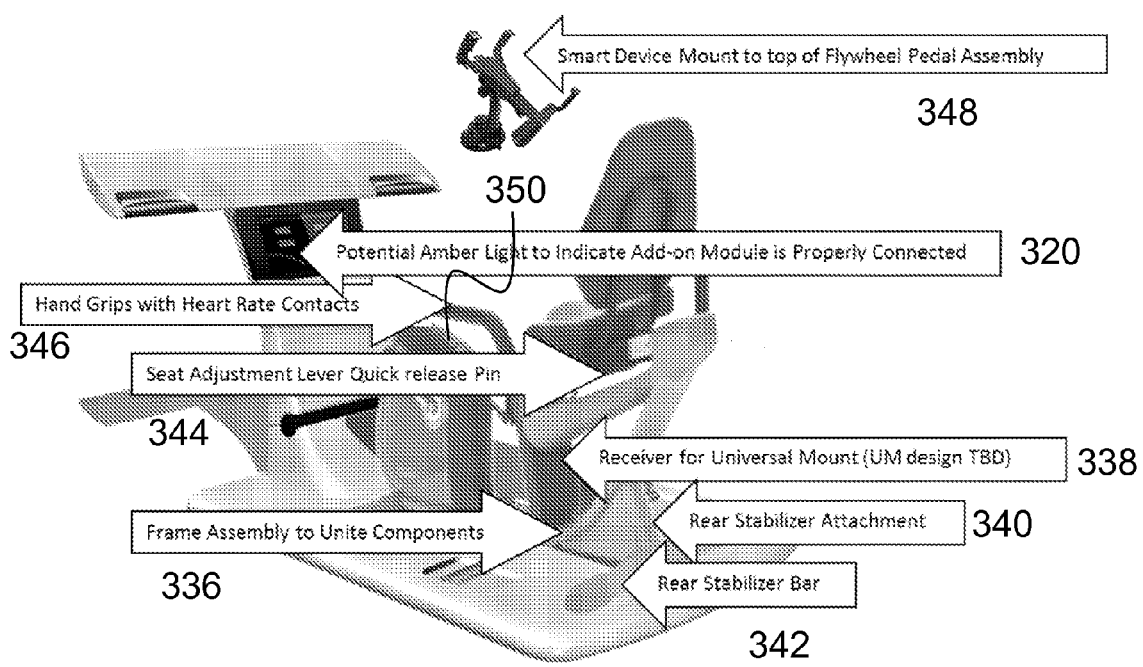
FIG. 5 is a perspective view illustration of a second configuration of the exercise device, according to an embodiment of the invention.

An interactive reconfigurable exercise device 300 is illustrated in FIGS. 3-5, and comprises a reconfigurable feedback-driven interaction portion which provides feedback to a user during a performance of at least one exercise program, such as physical, tactile or haptic feedback; a visual feedback portion which provides visual feedback—such as audio or video feedback—to the user relating to the performance of the at least one exercise program; and a controller which communicates with the reconfigurable interaction portion and visual feedback portion to control an amount of the feedback provided by the interaction portion.

Throughout this embodiment, the exercise device may also be referred to as a hardware platform, which in this embodiment is a mechanical-for-force transmission system that transmits resistance from one or more motors to upper and lower cables independently.

In one embodiment, the hardware platform 300 is embodied by a base 302, a tower 304 and a reconfigurable portion 306 which in this embodiment is a seat. The hardware platform 300 may employ a motor-controller 308 within the tower 304 or base 302 and one or more cable/pulley/spool motors 310 to provide resistance to a cable/pulley/spool 312 utilized by a user for exercise. Additionally, a tower indicator section 314 on the tower 304 and a corresponding software indicator control provide interactive resistance control through the motor controller 308. Separate take-up spools may be used to independently actuate each cable or pulley. A dashboard section 316 may be configured to dock, mount or retain the base unit 112. Wired or wireless connectors such as Bluetooth, NFC, USB or other connection types will provide communication with the base unit smart devices and the hardware platform 300. The Base Unit Smart devices may be smartphones and tablets, and may operate on a mobile operating system such as iOS or Android. Signals between the base unit and hardware platform 300 will be bidirectional.

The on-board motor controller 308 interacts with the hardware and software applications and serves as an interface controller that applies resistance to cables and electromagnets, and provides forced feedback based on user/app interaction. The hardware platform 300 may provide movement of the platform in an X, Y, or Z axis. As will be described in further detail below, the reconfigurable portion 306 is mounted to the base 302 on a universal mount 318 which is capable of being fitted with a plurality of different exercise modules to provide for the performance of different exercises.

The hardware platform is intended to assist in building strength, joint and muscle flexibility, range of motion of individual limbs, sense of balance and stability. It may also perform rehabilitation functions, sports and movement training, balance and other physical therapies.

Specific components of the hardware platform are listed below and illustrated in FIG. 4, including indicator lights 320 and a visual display 322 on the tower indicator section 314. As shown in FIG. 4, the cables 312 are gripped with cable handles 324, and the cables 312 may be mounted at different positions on the hardware platform, such as the lower cable handles 326 on the base 302. In one embodiment, direct current powers the electrical drive modules and the controller, although AC power may be used as well. A power supply is mounted within the tower, and standard household current connection plugs in from the tower.

All lights turn off when the machine is powered off. A built-in safety feature is that the hardware platform shuts off after five minutes of non-operation.

The onboard motor controller 308, as a sensor link, is responsible for actuating and measuring cable resistance and position of the cables 312, as well as controlling other resistance devices, such as electro magnets, enabling bidirectional communication with the hardware platform apps through attached/paired base unit smart devices.

Forced Feedback: An onboard motor controller program provides resistance in concert with apps. Forced feedback may be a tactile feedback technology, which takes advantage of the sense of touch by applying forces, vibrations, or motions to the user through the cables. In one embodiment, the hardware platform enables, at a minimum, weight settings with control over the right side and left side individually and in combination.

Bluetooth/USB: Wired or wireless connections to smart devices enable communication through the onboard motor controller 308 or other electronics, i.e., motherboard. The USB connection enables smart devices to be charged and serves as communication link.

Pairing: In one embodiment, establishing a connection between smart device/app and the hardware platform enables users to easily establish communication between the smart device and the on board motor controller (through Bluetooth or USB connector).

Calibration: Calibration operations may be performed to assure that the apps and motor controller functions are connected and are operational in a synchronous real time environment. Real time response between apps and the resistance devices on the hardware platform is imperative for acceptable user experience.

Universal Mount: The universal mount 318 on the base 302 attaches and secures a "removable" seat 306 and other future modules. The universal mount will also accommodate a wire harness with electric power and communications with the motor controller for future modules. The modules may include other types of exercise devices, including an exercise bar 328 or leg strap 330, but also including bicycles, skis, oars, or even a baseball bat, golf club, tennis racquet, etc.

Tower Smart Device Dock 316: Located in the center space between the cable handles on the tower 304, the dock 316 provides a secure, no-slip holder for smart phones and tablets. In addition, it may house a connector such as a USB connector.

Handle Drop Safety Consideration: In one embodiment, iIf a user drops any cable handle while under tension, the resistance stops momentarily and then slowly retracts the handles to their stored position.

Folding Hinge 332: A folding hinge 332 enables the folding and unfolding of the tower 304. The hinge 332 should lock securely to counter the pull exerted by the cables. Any wiring routed to the tower that is exposed when folded is to be protected from accidental pinching or other actions detrimental to Hardware platform safety and operation.

FIG. 5 illustrates an alternative configuration of the hardware platform 300 with a bicycle module 334 connected via the universal mount 318. The bicycle module 334 includes a frame assembly 336 to unite the base 302 with the bicycle module 334 and a receiver 338 for the universal mount 318. A rear stabilizer attachment 340 and a rear stabilizer bar 342 may also be incorporated into the bicycle module 334 to provide stability during operation. The bicycle module 334 may also be configured with a seat adjustment pin 344 to adjust the seat, and hand grips 346 with heart rate contacts to monitor a user's heart rate during an exercise. FIG. 5 also illustrates one embodiment of a smart device base unit mount 348 that is configured to mount to a flywheel pedal assembly 350 on the bicycle module.

IV. General Description and Operation

In one embodiment, exercise is achieved by pulling one or two cable handles 324 under a resistance load. In one embodiment, the cable handles 324 are located at four positions, two upper cable handles 324 located in the tower 304 and two lower cable handles 326 on the base platform 302 (floor). In one embodiment, each side may provide up to 200 pounds on each motor, providing a total of 400 pounds of weight resistance.

One embodiment of the hardware platform machine is composed of the following features described below:

The Hardware platform 300 consists of an upright body (tower 304 and dashboard 316) with resistance sources, the removable seat assembly 306 and the base platform 302. The base platform 302 is supported on two casters; it is sufficiently narrow for transporting the machine through 30" wide doors.

The seat 306 can be unfolded to form a bench for exercises in various orientations. The seat is locked in place at various heights to accommodate short and tall users. The removable seat assembly includes a reclined backrest for support and bracing during specific exercises.

A dock 316 for placing a base unit 112, such as a smart phone or tablet, will be located in the tower 304. Communication with the base unit smart device 112 will be via Bluetooth or a USB connector also located in the tower 304.

The exercise bar 328 fits into either the upper cable handles or lower cable handles. The exercise bar accessory 330 can be securely attached to either the upper cable handles 324 or lower cable handles 326. The leg strap accessory 330 is attached to the user's ankles for leg exercises.

V. Motor Control

Users connect their paired and calibrated base unit smart device 112 to the tower and select an interactive program on an application running on the base unit 112 designed to work with the hardware platform 300. The program may be stored in the program database 114 at the remote cloud server 118 and accessed over a network. Indicator lights 320 provide status of power, Internet connectivity, and hardware platform operational readiness. Selected apps on the smart devices provide visual displays and produce/react to bidirectional signals relayed to the app through the hardware platform onboard motor controller that provides multiple types of feedback to the user by responsive hardware platform cables 312. In another embodiment, other resistive devices may be employed to provide alternative types of feedback, such as electromechanical controlled or servo-controlled add-on modules. The result is the change in resistance consistent with the smart device displays in real-time.

Electrical Cable Drive

In one embodiment, the electrical drive and the motor control interface for generating the resistance force are positioned in the base of the tower structure 304. Each of the two upper cables attached to the upper cable handles 324 may reel out from the tower 304 approximately five to six feet. The two lower cables attached to the lower cable handles 326 may reel out approximately six to nine feet. Cable reels, pulleys, spools, a gear or transmission, and the servomotor with sensors are tied together, perhaps on a common or separate axis, and they compose the electrical drive module. All of these components are known as the electrical cable drive system.

In operation, variable current, and thereby torque, is applied to the servomotor. These affect the cable resistance force, while unreeling and reversing the cable.

The motor controller provides cable resistance, distance and velocity communication to the smart device apps, and responds with feedback (forced, haptic, visual, audio, etc.) to application outputs to affect resistance and direct difference exercise regimes. One or more sensors within the motor controller sense the extended length of cable per millimeter. The sensors are also integral to measure speed and distance of cable movement i.e., how rapidly and how far the cable moves in both directions, as well as the angle of the cable. These bidirectional signals will be responsive to user interaction with apps with real-time interactivity and may be coupled with a motion tracking device to help determine, along with the motor controller information, whether the exercise is being performed correctly In one embodiment, the electrical cable drive will have latency under 100 ms.

The user is able to select different exercise regimes using an application running on the smart device, which then controls the motor controller. The motor controller also provides feedback to the smart device and the application on the device as to the performance of the user with the equipment. The performance of the cable drive will eliminate (a) any backlash or dead stretches during reel-out and (b) cogging sensation, while applying smooth force to the handles.

VI. Cable Forces

In one embodiment, the maximum bi-directional forces on the cable at the handle attachment location are 200 lbs. per side when pulled simultaneously or 400 lbs. when pulled separately from the bottom handles and for the upper handles.

When pulled simultaneously, both the upper and lower cables will provide a maximum bi-directional force of 200 lbs. per handle for a total of 400 lbs. When any one of the four cables is pulled by itself, it will provide a maximum bi-directional force of 200 lbs. Various contributors of friction, including from the drive assembly itself, shall be included in these values. In one embodiment, the net lowest force setting may be 2 lbs. In one embodiment, friction force at the cable termination shall not exceed 2% of used force during cable extension and 2.5% of force during retraction. The maximum force in both directions may be equal, or the retraction force may be set to a lesser or greater value, as set by the application controlling the motor controller located in the tower structure. The forces in both directions may change linearly or within a prescribed curve. The force levels may reset themselves for a specific exercise. The force level may then be maintained, once motion has slowed and arrived at standstill.

The force level may change and direction of force shall change with slack-off of motion to zero prior to reverse cable motion. The resistance level can be set to zero until the handles are positioned for any specific exercise to be programmed into the motor controller. The force on any handle will drop to zero if a handle is released suddenly by the user.

VII. Dimensions and Range of Motion

In one embodiment, the dimensions of the exercise device may be provided as follows: Platform width max.: 27.5 inches; Platform base length: 60-72 inches (The platform base may need to have the length increased in order to accommodate future modules.); Overall length (use): 73-85 inches; Overall length (for stowing): 64-76 inches; Overall height (stowed): 15 inches; Platform thickness: 2 inches; Height from platform top to upper cable exit: 30 inches; Usable cable extension length: 108 inches for lower cable and 72 inches for upper cable.

Drive Motors

In one embodiment, the electrical drive motor or motors 310 shall be mounted within the tower structure, although the motors may be located in any part of the hardware platform 300 depending on the configuration of the platform or the type of workout device attached with the platform.

The drive motor assembly, when installed, shall permit heat dissipation within the tower through conduction, convection, louvered ventilation, or other means. Tower surfaces shall not generate heat beyond 95 degrees F., under the environmental conditions. The drive motor and cabling shall be electromagnetically shielded, when installed.

All cable wiring harnesses shall terminate in reliable connectors at the mating interfaces of modules. Such cabling includes power, control and auxiliary equipment routing including smart devices, as well as communication with all external apps, via Bluetooth or USB.

The drive motor assembly is to fit within the tower confines, which are planned to be 4×12 inches or less. The modular approach permits easy access and exchange of the drive motor or drive motor components/modules without affecting the installed force cable assembly. For design considerations, the motor control board(s), any potential motherboard, or other circuitry could be mounted behind the LED indicator light panel for easy maintenance.

Mobility

Since the end user will operate the hardware platform machine in bedrooms and other living environments, it is suited for simple fold-up and move for stowage, also transporting through nominally 30-inch wide door openings (effectively 28 inches).

The machine, as assembled for transport, shall move on two rollers, which are mounted under the platform proper at the tower end. Each roller shall have a capacity of 150 lbs. and be non-marking on floors or carpets. The casters shall be effectively contacting the ground for rolling, when the platform is tilted upward 30-45 degrees.

Stiffness and Backlash

The user wants smooth extension and retraction of the cable. Excessive dither and jitter, backlash and structural flexure are objectionable, however subjective.

With the user standing anywhere on platform and applying 400 lbs. force on one or two cable handles, the tower and platform flexure shall not be perceptible by the user, i.e. not to exceed ½ inch total.

Note that for structural and component design, the stiffness criteria (rather than strength) may determine design and sizing. Modular interfaces may need to incorporate shear locators and shear connectors to provide rigid mounting under load, rather than relying only on bolted or welded assembly methods.

All fasteners will have self-locking features continuing to function after five assembly operations. All electrical harness and other connectors shall function reliably after five connections and disconnections.

VIII. Interaction Portion—Platform and Mount

As illustrated in FIGS. 3-5, the hardware platform 300 is designed for easy attachment to the Universal Mount 318 on the Hardware Platform. The attachment process includes attaching the Wire Harness from the hardware platform and securing modules, such as the bicycle module 334 with a Key Pin or other securing method, such as slots, pins, or retractable pins which fit into the slots. Seat adjustments will be an easy to use incline ramp to increase and decrease the distance from the pedals.

Performance

The hardware platform machine is planned as a base platform and allows for upgraded add-on features over time. These considerations are included in the Onboard Motor Controller Functional Specs below.

Onboard Motor Controller Functional Specs

The function and features of the hardware platform onboard motor controller 308 shall be as follows:

1. Bi-directionally control and accurately measure cable resistance, force, direction, velocity, and position/angle levels from the four points of handles on the upper tower and lower portions of the base handles.

2. Communicate with smart devices using Bluetooth and USB

3. Easily pair and calibrate with smart device phones and tablets

4. Communicate and respond to app outputs for forced feedback with latency under 100 ms 5. Measure cable extension and retraction by millimeters with accurate fidelity 6. Maximize measurement per second with latency under 100 ms 7. Maximize resistance, force, direction, velocity, and position from app output The Onboard Motor Controller 308, as a sensor link, is responsible for actuating and measuring cable resistance and position, as well as controlling other resistance devices, such as electro magnets, enabling bidirectional communication with Hardware platform apps through attached/paired smart devices.

Smart Device Communication

The Motor Controller 308 must communicate with the base unit 112, including smartphones and tablets, using any proprietary or known operating systems, including iOS and Android operating systems. Future operating systems may include Windows and others.

Seat/Bench Positions

The removable seat/bench assembly shall be finely height adjustable and safely lockable from 16 to 20.5 inches above the platform in minimum increments of 0.5 inches and firmly attached to the universal mount with mounting pins. The seat shall support a maximum weight of 300 lbs. The seat shall not move perceptibly from an upward or sideways exercise force of 200 lbs. Seat should rotate 360 degrees with locks at 180-degree positions to facilitate using the seat back as a part of exercise back support when required.

The forward portion of the bench shall be settable in an upward rotated position to enable a person to stand while exercising in between bench and tower. The seat should be designed to be easily removable.

The bench/seat top surface shall be cushioned and not feel unpleasant to touch when exposed to perspiration.

A universal seat mount 318 will be designed on the hardware platform 300 to accept future modules, as well as the base model seat. The universal seat connector will include both a mechanical connector and a wire harness with the following input/output: 110V power, 48V DC power. All cable wiring harnesses shall terminate in reliable connectors at the mating interfaces of modules. Such cabling includes power, control and auxiliary equipment routing including smart devices and apps and Bluetooth and USB. In one embodiment, the universal seat mount 318 could have a plurality of contact points which each represent a different type of device. For example, if five total contact points are available, a certain type of seat mount may use three of the connections in a specific pattern to identify which device is being connected, while another type of mount may use three connections in a different pattern, or four connections instead of three.

User Exercise Assist and Accessories

In one embodiment, cable attached accessories include: handles attached to cable that are easily replaceable and sold as a replacement accessory; one exercise bar, approx. 40" long; and two foot straps for leg exercises.

The machine shall be powered by nominally single phase 110+/−10 Volt, 60+/−5 Hz and selectable 220+/−10 Volt 50+/−5 Hz. A grounding connection shall be included.

Two separate power cord connectors shall service the two types of power. This facilitates adaptation of plug-in connection to various countries' particular connection requirements, by simply supplying an appropriate power cord.

Other foreign power compatibility requirements may be added.

The machine shall tolerate and survive without damage brownout conditions and momentary spikes and variations in voltage and frequency from nearby lightning and other such effects.

Drives, Controls/Computer and Auxiliary Devices

Considerations for drives, controls/computer and auxiliary devices will focus in two distinct areas. The first area is the collective drives, controls/computer and auxiliary devices in the hardware platform that enable motor controller and user app outputs from and inputs to users' smart devices to direct or record, as directed, the different exercise regimes with variable: resistance, force, direction, velocity, and position/angle along with forced feedback. Bi-directional signals will be responsive to user interaction with apps with real-time interactivity.

A sensor will detect the extended length of cable in each of the four cables measured in millimeters. In addition, the sensor is used for speed sensing, i.e., how rapidly the cable moves in both directions. This input will be communicated to the smart device via Bluetooth and USB connections.

The second area is connections that are in a ready state for auxiliary modules. Power to the auxiliary module, communication for bi-directional control signals to and from smart devices and the auxiliary module, and real time enabled response for resistance settings is inherent in both the stand alone hardware platform and in conjunction with the modules. In addition, the signal for bi-directional communication will enable signals from the hardware modules concurrent with the hardware platform to enable, as an example, resistance and forced feedback to the pedals attached to the exercise bike module, as well as to the hand held cables in the hardware platform.

If needed for limiting spikes, a separate transformer may supply the motor controller as powering motor, smart devices, and add-on modules.

Sufficient current shall be available for all electrical and electronic equipment, without making changes for the hardware base platform model, including any auxiliary devices and add on modules.

IX. Method of Providing Resistance and Feedback

Figure 6:
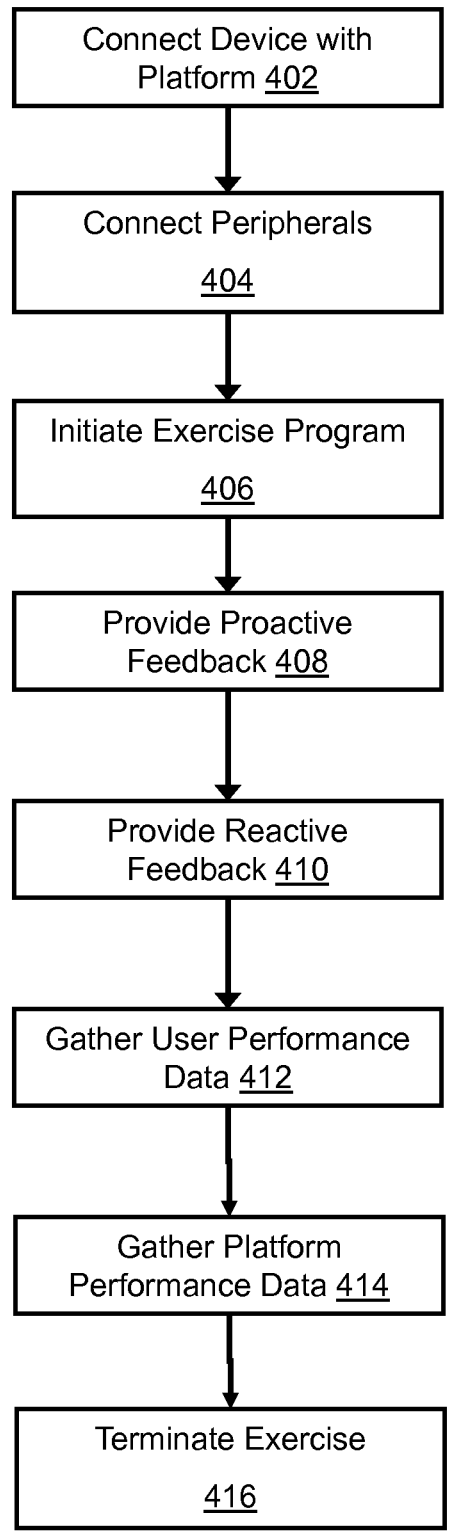
FIG. 6 is a flow diagram illustrating an example process for executing an interactive exercise system according to an embodiment of the invention.

FIG. 6 is a flow diagram illustrating an example process for executing an interactive exercise system according to an embodiment of the invention. In a first step 402, a base unit smart device is connected with the hardware platform, and in a second step 404, any peripheral devices such as displays or wearable monitoring devices are connected with the hardware platform or base unit. Next, in step 406, an exercise program is initiated at the smart device and executed by the hardware platform. In step 408, during the performance of the exercise program, proactive feedback is provided from the hardware platform to the base unit based on the user's performance. In step 410, reactive feedback is then provided from the base unit to the hardware platform in response to the proactive feedback from the hardware platform. User performance data may be gathered in step 412 and stored at the base unit or transmitted to a remote cloud server for further analysis in order to revise the exercise program based on the user's performance. In step 414, the platform performance data may be gathered and transmitted to the base unit and remote server as well, for understanding the user's performance during the exercise program and for adjusting the settings of the hardware platform and exercise modules for future exercise programs. The exercise program may then be terminated in step 416.

X. Computer-Enabled Embodiment

Figure 7:
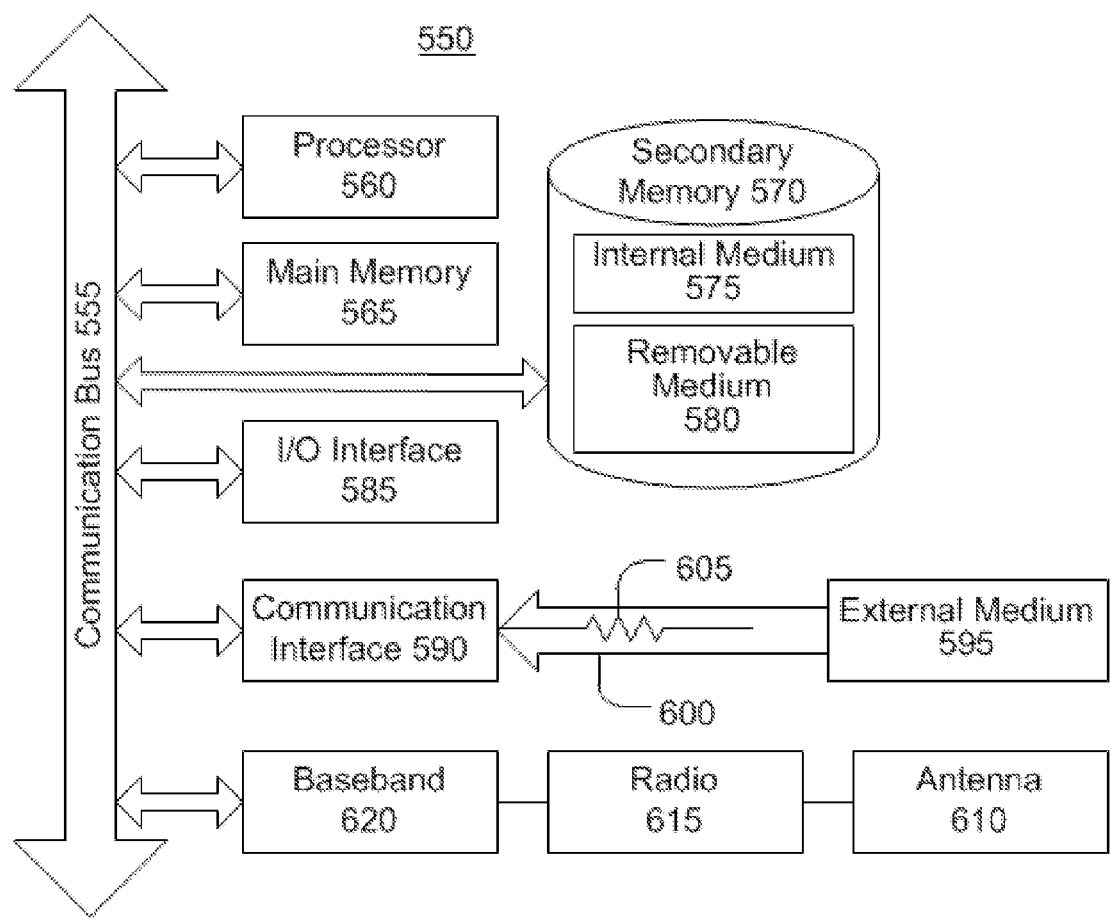
FIG. 7 is a block diagram illustrating an example wired or wireless processor enabled device that may be used in connection with various embodiments described herein.

FIG. 7 is a block diagram illustrating an example wired or wireless system 550 that may be used in connection with various embodiments described herein. For example the system 550 may be used as or in conjunction with an interactive-feedback exercise device as previously described with respect to FIGS. 1-6B. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a flash memory (USB) drive, reprogrammable and removable firmware, EEPROM, a compact disc ("CD") drive, a digital versatile disc ("DVD") drive, etc. The removable medium 580 is read from and/or written to in a well-known manner. Removable storage medium 580 may be, for example, a flash memory (USB) drive, reprogrammable and removable firmware, EEPROM, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570 in any smart device, firmware or other device. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. An interactive exercise system comprising:
   an exercise device configured to provide physical feedback to a user;
   a portable electronic device in communication with the exercise device to communicate instructions to the user for an exercise program and provide feedback to the exercise device regarding user performance; and
   a wearable electronic device attached with the user and in communication with at least one of the exercise device or portable electronic device to transmit user activity;
   wherein the exercise device provides physical feedback to the user based on the feedback provided by the portable electronic device;
   wherein the physical feedback is tactile feedback; and
   wherein the feedback from the portable electronic device is displayed to the user.

2. The interactive exercise system of claim 1, wherein the exercise device further comprises a motor controller to translate the exercise program and the feedback regarding user performance into haptic feedback to the user.

3. The interactive exercise system of claim 1, further comprising a display device in communication with at least one of the exercise device or portable electronic device to display a graphical user interface to the user.

4. The interactive exercise system of claim 3, wherein the display device is a virtual display device which displays a virtual environment to the user.

5. The interactive exercise system of claim 4, wherein the virtual environment is related to the performance of the exercise program.

6. The interactive exercise system of claim 1, wherein the performance of the exercise program is tracked and utilized to revise the exercise program.

7. The interactive exercise system of claim 1, wherein the physical feedback is provided in real-time during the performance of the exercise program.

8. The interactive exercise system of claim 1, wherein the wearable electronic device includes a sensor which senses at least one of: movement, degree of motion, heart rate and blood pressure.

9. The interactive exercise system of claim 8, wherein the wearable electronic device is incorporated into an article of clothing.

10. The interactive exercise system of claim 1, further comprising a user authentication device incorporated into at least one of the exercise device, portable electronic device, display device or wearable electronic device which authenticates the user to the exercise system.

11. An interactive reconfigurable exercise device, comprising:
   a reconfigurable feedback-driven interaction portion which provides physical feedback to a user during a performance of at least one exercise program, wherein the physical feedback is tactile feedback and is based on feedback regarding user performance received from a wearable electronic device attached with the user;
   a visual feedback portion which displays visual feedback to the user relating to the performance of the at least one exercise program; and
   a controller which communicates with the reconfigurable interaction portion and visual feedback portion to control an amount of the physical feedback provided by the interaction portion.

12. The exercise device of claim 11, wherein the physical feedback is proactive and reactive.

13. The exercise device of claim 11, wherein the physical feedback is provided in real-time during the performance of the at least one exercise program.

14. The exercise device of claim 11, further comprising a portable electronic device in communication with the exercise device to communicate instructions to the user for an exercise program and provide feedback to the exercise device regarding user performance.

15. The exercise device of claim 11, wherein the interaction portion may be reconfigured to allow a user to perform a plurality of different exercises.

16. The exercise device of claim 15, wherein the interaction portion may be reconfigured to provide an exercise including at least one of: bicycling, rowing, running, skiing, climbing, swinging, surfing and wakeboarding.

17. The exercise device of claim 11, wherein the performance of the exercise program is tracked and utilized to revise the exercise program.

18. The exercise device of claim 11, where the device is utilized for physical rehabilitation.

19. The exercise device of claim 18, wherein the exercise device is linked with at least one additional exercise device to enable simultaneous participation by multiple users.

20. The exercise device of claim 11, wherein the physical feedback is haptic feedback.

* * * * *